6/7/83 XR 4,386,612

United States Patent [19]

Röder et al.

[11] 4,386,612

[45] Jun. 7, 1983

[54] ULTRASONIC TRANSMITTER

[75] Inventors: Ulrich Röder, Munich; Harald Seidlitz, Eching; Christof Scherg, Munich, all of Fed. Rep. of Germany

[73] Assignee: Gesellschaft für Strahlen-und Umweltforschung mbH München, Neuherberg, Fed. Rep. of Germany

[21] Appl. No.: 308,938

[22] Filed: Oct. 5, 1981

[30] Foreign Application Priority Data

Oct. 4, 1980 [DE] Fed. Rep. of Germany ....... 3037641

[51] Int. Cl.³ .......... A61B 6/00

[52] U.S. Cl. .......... 128/660; 73/632; 73/642

[58] Field of Search .......... 73/632, 642, 644; 128/660, 661, 662, 663; 310/335, 336, 337; 367/150, 152, 166

[56] References Cited

U.S. PATENT DOCUMENTS 4,153,894 5/1979 Alphonse et al. .......... 73/644
4,276,885 7/1981 Tickner et al. .......... 128/660

OTHER PUBLICATIONS

Meltzer et al., "The Source of Ultrasound Contrast Effect;" Journal of Clinical Ultrasound; Apr. 1980, pp. 121-127.

Anderson et al., "A New Noninvasive Technique for Cardiac Pressure Measurement II: Scattering from Encapsulated Bubbles;" Conference Report: Noninvasive Cardiovascular Measurements, Stanford, CA., Sep. 1978, pp. 121-127.

*Primary Examiner*—Richard J. Apley
*Assistant Examiner*—George Yanulis
*Attorney, Agent, or Firm*—Spencer & Kaye

[57] ABSTRACT

In an ultrasonic wave transmitter for generating spatially incoherent ultrasonic radiation, which transmitter includes a source of ultrasonic acoustic radiation, there are provided a member holding a fluid medium in a region exposed to the acoustic radiation, a plurality of particles immersed in the medium and having a diameter of the order of magnitude of the wavelength of the acoustic radiation and an acoustic radiation impedance different from that of the medium, and a device for subjecting the particles to an irregular movement in the medium and within the region.

7 Claims, 2 Drawing Figures

ULTRASONIC TRANSMITTER

BACKGROUND OF THE INVENTION

The present invention relates to an ultrasonic transmitter for generating incoherent, or diffuse, ultrasonic radiation.

Ultrasonic acoustic imaging techniques, in contradistinction to conventional echo processes for medical diagnosis, serve to provide optical representations of differences in attenuation of acoustic energy in the human body.

For this purpose, the subject is penetrated, or insonified, by an ultrasonic acoustic wave and a suitable lens with large aperture images, or focusses, the ultrasonic information on a detector array. Such a method is disclosed, for example, by J. F. Havlice et al. in Acoustical Holography, Volume 7, edited by L. W. Kessler, Plenum Press, 1977, at pages 291–305.

Since it was found that a coherent image made with but one ultrasonic transmitter was unable to furnish reliable images for diagnostic purposes, Havlice et al. employed, in a further development of the transmission method, twenty to thirty independent ultrasonic transmitters and thus realized a partially spatially incoherent insonification of the subject.

The resulting ultrasonic images are of usable quality, particularly for the imaging of tendons and vessels in extremities. However, for images in the upper abdominal region through the body, the long path traversed has an adverse influence on the quality of the image.

In principle, an ultrasonic transmission arrangement includes a transmitting member with condenser lens in front of the subject and a receiving member with objective lens behind the subject.

The transmitting member for diffuse insonification includes a plurality of sound sources whose emitted sonic fields are statistically independent of one another. Due to the coherence conditions known in optics, regions with an area $F_{El}$ must be considered to be spatially coherent elementary sources according to equation (1).

$$F_{El}=\lambda^2 A^2/F_{Ap} \qquad (1)$$

where $\lambda$=wavelength of the ultrasonic radiation

A=transmitter—condenser distance, and $F_{Ap}$=area of the condenser lens aperture.

It would therefore make no sense to further reduce the area of the elementary sources. The maximum number, $N_{max}$, of mutually incoherent elementary sources in an expanded source then results from equation (2).

$$N_{max}=F_{Source}/F_{El}=F_{Ap}\,F_{Source}/\lambda^2 A^2 \qquad (2),$$

where $F_{Source}$ is the area of the expanded source.

In order to realize as incoherent as possible an insonification with an expanded source, N elementary sources of the size indicated in equation (2) should be used, where N is a large number. Each one of these individual sources produces an image in the detector plane, the image information of interest always being the same and the noise resulting from scattering or from interference effects changing from source to source. From statistical considerations it follows that the signal-to-noise ratio which is proportional to the square root of the number N of elementary sources increases up to a maximum value for which N has the value given by equation (2). For a conventional transmission system, the following parameters apply: f=2 MHz ($\lambda$=0.75 m), A=50 cm, source diameter=condenser lens aperture diameter=20–25 cm.

From this, it follows that $N_{max}\cong 10^4$ with respect to the transmitter area.

A system having the above-mentioned parameters should thus include, for diffuse insonification, approximately $10^4$ independent individual transmitters so as to obtain an image which is as free from interference as possible. The system produced by Havlice et al. uses, as a maximum, 30 independent individual transmitters with each ultrasonic transmitter having its own actuating unit and amplifier unit. An expansion of the number of transmitters by 1 or 2 orders of magnitude based on this system appears impossible.

SUMMARY OF THE INVENTION

It is therefore an object of the present invention to provide a practical ultrasonic transmitter of the above-described type which can have this number N of individual sources.

The above and other objects are achieved, according to the invention, in an ultrasonic wave transmitter for generating spatially incoherent ultrasonic radiation, which transmitter includes a source of ultrasonic acoustic radiation, by the provision of means holding a fluid medium in a region exposed to the acoustic radiation, a plurality of particles immersed in the medium and having a diameter of the order of magnitude of the wavelength of the acoustic radiation and an acoustic radiation impedance different from that of the medium, and means for subjecting the particles to an irregular movement in the medium and within the region.

According to the present invention, coherent sound arriving from a primary source is thus scattered at many small stray particles whose dimensions lie in the order of magnitude of the wavelength employed. If these particles are in statistically random motion, they act as independent elementary sources. The speed of movement of the particles is selected so that during the time available for detecting the intensity of an image point, as many granulation patterns as possible are produced in the image plane.

Thus there is produced, for a transmission arrangement, an insonification which is significantly more complete and more spatially incoherent, or diffuse, than in the prior art methods. This significantly improves the signal-to-noise ratio and at the same time reduces the influence of scattering within the body to be examined. This is of significance for an ultrasonic image made through the body.

DESCRIPTION OF THE PREFERRED EMBODIMENTS

Figure 1:
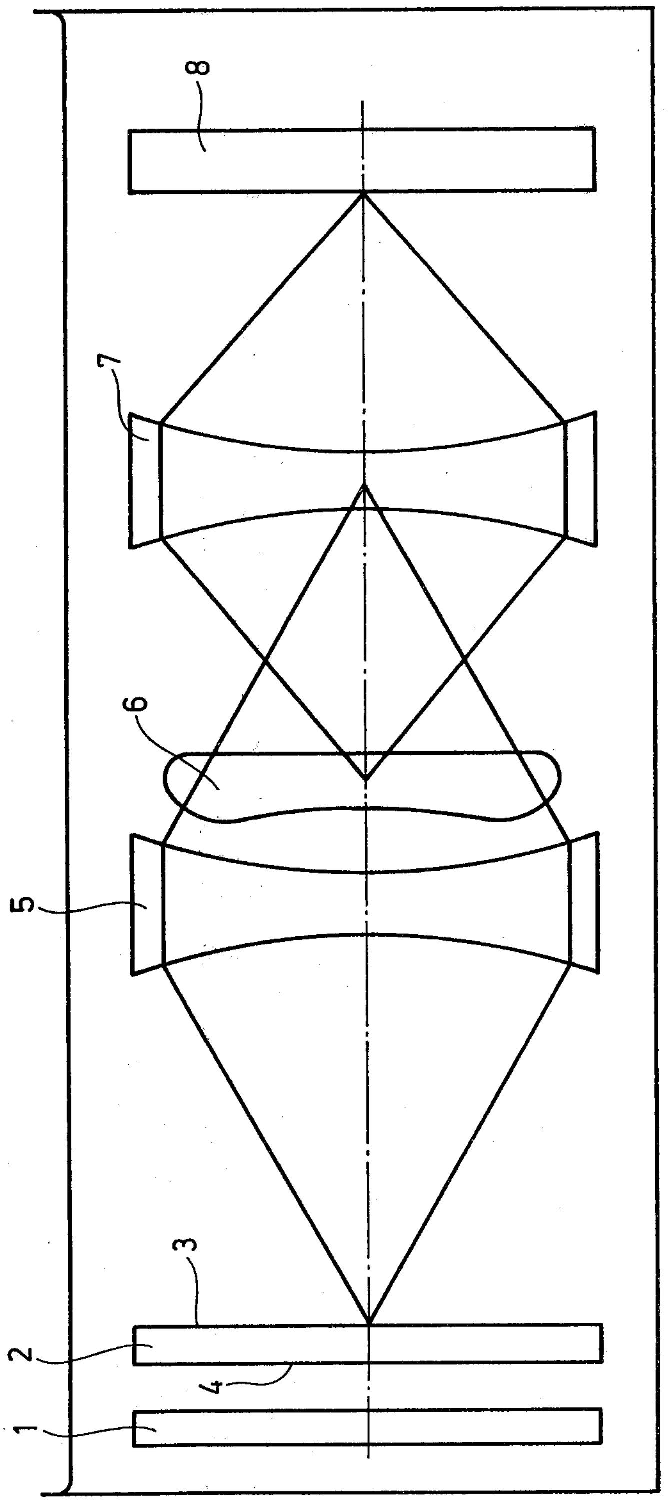
FIG. 1 is a schematic side view of an ultrasonic imaging system embodying the invention.

FIG. 1 is a schematic representation of an ultrasound transmission arrangement which could also be modified without difficulty into a back scatter arrangement, similar to the transmitted light method and the reflected light method, respectively, in optics, and could be operated as such. A large-area coherent transmitter 1 transmits sound into a turbulence chamber 2, one embodiment of which is shown in detail in FIG. 2. The chamber 2 contains particles 9 which constitute the starting points of spherical waves which in their entirety, because they constitute a multitude of sources, generate incoherent radiation which emanates from a large area. The transmitter 1 has the effective surface area $F_{source}$.

The incoherent, or diffuse, radiation emanating from the radiation exit window 3 of the turbulence chamber 2 is directed by means of the condenser lens 5, with an aperture area $F_{AP}$, onto the subject 6. It penetrates the subject 6 and is then imaged by means of the objective lens 7 onto the detector array 8. The turbulence chamber 2 used in the transmission process has an entrance window 4 as well as the exit window 3. In the case of measuring according to the reflected light method, only an entrance window is needed through which the scattered sound generated in the turbulence chamber 2 leaves again.

Figure 2:
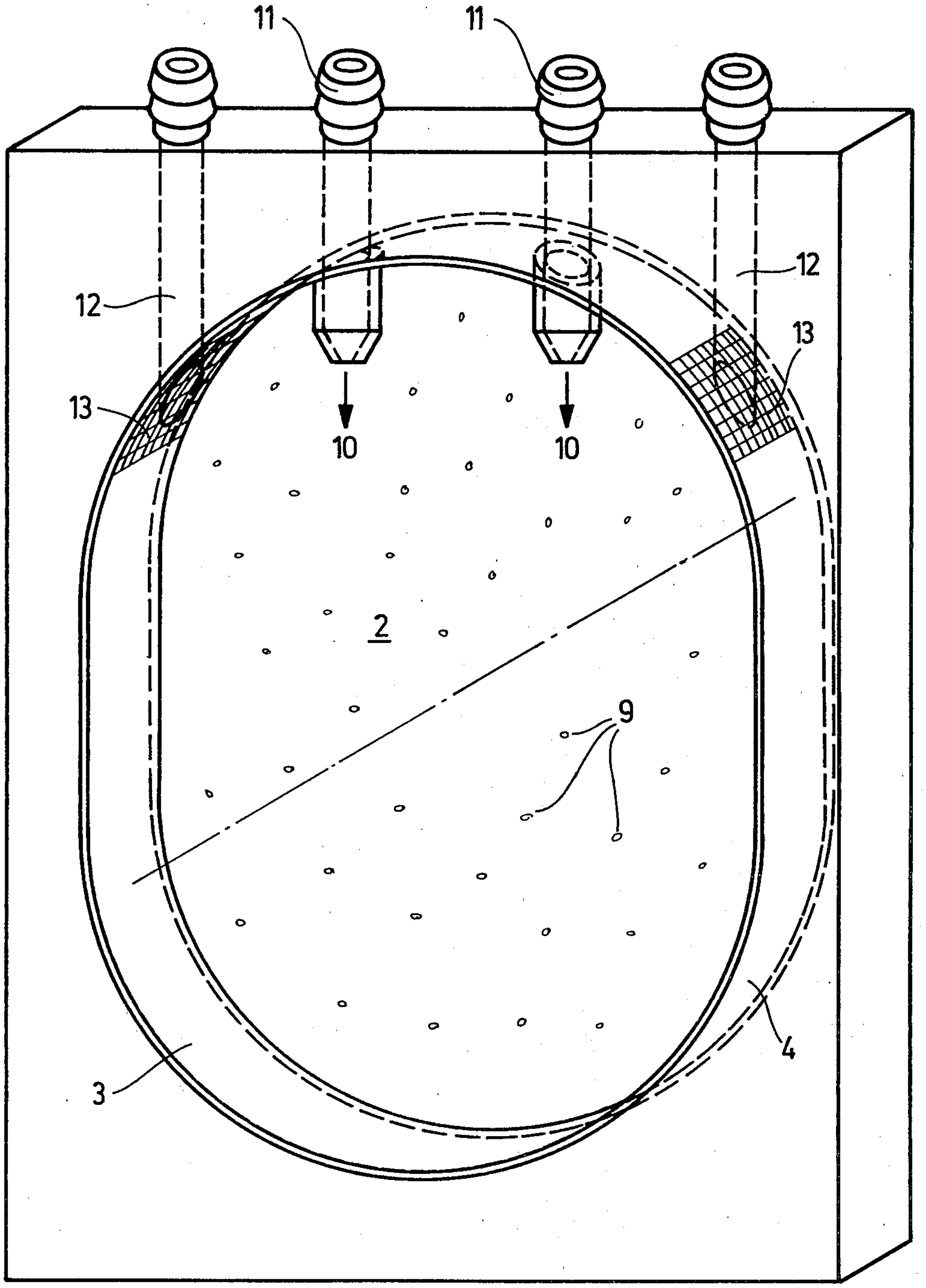
FIG. 2 is a perspective view of a preferred embodiment of a transmitter member according to the invention.

FIG. 2 shows the structure of such a turbulence chamber 2 for a system operating according to the transmission method. The turbulence chamber 2 with its entrance and exit windows 3 and 4 made of Plexiglas or polystyrene is partially filled with polystyrene particles 9 whose diameters are dimensions in the range of approximately 1 mm for an ultrasound frequency of about 2 MHz. Water 10 is caused to flow through the chamber 2 in as turbulent a manner as possible. The inlet nozzles 11 supply the water 10 at high speed, e.g. in respectively different directions, into chamber 2. Screens 13 are disposed in front of the two outlet passages 12 to prevent the particles 9 from leaving the chamber 2.

Even this simple arrangement permits unorderly movement of the polystyrene particles 9 at a speed of the order of magnitude of 1 m/sec. Due to the difference in impedance between the polystyrene particles 9 and the water 10, an incoming ultrasonic wave will be scattered at every polystyrene particle 9 and will thus be the starting point of a new elementary wave. The summation of these elementary waves produces a granulation pattern which constantly changes due to the motion and, when averaged over a sufficiently long period of observation, produces a spatially incoherent sonic field. This effect can be additionally improved by combining the entrance and exit windows 4 and 3 of the turbulence chamber 2 with additional ground glass focusing screens, or by employing such materials for the windows themselves.

The concentration of the polystyrene particles 9 with 0.5–2 mm diameter is 10,000–10 particles/$cm^3$ in chamber 2. The thickness of the volume of liquid in chamber 2 is 2.4 cm; the volume is 600 $cm^3$. The thickness of windows 3 and 4 is 2 mm. They are made of polystyrene. The flow rate of liquid into and out of the chamber 2 to produce the desired level of turbulent flow therein is 5 liter/min.

It will be understood that the above description of the present invention is susceptible to various modifications, changes and adaptations, and the same are intended to be comprehended within the meaning and range of equivalents of the appended claims.

What is claimed is:

1. In an ultrasonic wave transmitter for generating spatially incoherent ultrasonic radiation, said transmitter including a source of ultrasonic acoustic radiation, wherein the improvement comprises: means holding a fluid medium in a region exposed to the acoustic radiation; a plurality of particles immersed in said medium and having a diameter of the order of magnitude of the wavelength of the acoustic radiation and an acoustic radiation impedance different from that of said medium; and means for subjecting said particles to an irregular movement in said medium and within said region.

2. An arrangement as defined in claim 1 wherein said means holding a fluid medium comprise a chamber enclosing said region and containing said medium and said particles, said chamber having at least one window disposed for passage of spatially incoherent radiation from said region.

3. An arrangement as defined in claim 2 wherein said window has an area corresponding to that of the acoustic radiation source.

4. An arrangement as defined in claim 2 wherein said means for subjecting said particles to an irregular movement comprise at least one inlet and one outlet associated with said chamber for respectively introducing said medium into and conducting said medium away from said region.

5. An arrangement as defined in claim 2 wherein said at least one window is constituted by a translucent ground glass sheet.

6. An arrangement as defined in claim 1 wherein said means for subjecting said particles to an irregular movement comprise means for imparting a turbulent movement to said medium.

7. An arrangement as defined in claim 1 wherein said medium is water and said particles are made of polystyrene.

* * * * *

UNITED STATES PATENT AND TRADEMARK OFFICE
CERTIFICATE OF CORRECTION

PATENT NO. : 4,386,612

DATED : June 7th, 1983

INVENTOR(S) : Ulrich Röder et al

It is certified that error appears in the above—identified patent and that said Letters Patent is hereby corrected as shown below:

In the heading of the patent, under [75] Inventors:, line 3, after "Munich,", add the fourth inventor's name and city to read --Hans Brettel, Munich,--.

Signed and Sealed this

*Sixteenth* Day of *August 1983*

[SEAL]

*Attest:*

GERALD J. MOSSINGHOFF

*Attesting Officer* *Commissioner of Patents and Trademarks*